United States Patent [19]

Northrop

[11] 4,197,856
[45] Apr. 15, 1980

[54] ULTRASONIC RESPIRATION/CONVULSION MONITORING APPARATUS AND METHOD FOR ITS USE

[76] Inventor: Robert B. Northrop, Chaplin St., Chaplin, Conn. 06235

[21] Appl. No.: 894,695

[22] Filed: Apr. 10, 1978

[51] Int. Cl.$^2$ .............................................. A61B 5/08
[52] U.S. Cl. ...................... 128/660; 128/721
[58] Field of Search .......... 128/2 R, 2 S, 2 V, 2.05 Z, 128/DIG. 29, 660, 721; 340/3 D, 560, 573

[56] References Cited

U.S. PATENT DOCUMENTS

| | | | |
|---|---|---|---|
| 3,631,849 | 1/1972 | Norris | 128/2.05 Z X |
| 3,763,851 | 10/1973 | Haff et al. | 128/2.05 Z |
| 3,768,487 | 10/1973 | Rose | 128/2.05 R X |
| 3,802,417 | 4/1974 | Lang | 128/DIG. 29 X |
| 3,875,929 | 4/1975 | Grant | 128/2 S |
| 3,938,500 | 2/1976 | Simmons | 128/2 Z |
| 3,948,248 | 4/1976 | Zuckerman et al. | 128/2 V |
| 3,993,995 | 11/1976 | Kaplan et al. | 343/7 ED |
| 4,122,427 | 10/1978 | Karsh | 128/2 V X |

FOREIGN PATENT DOCUMENTS

1439383  6/1976  United Kingdom ............ 128/DIG. 29

OTHER PUBLICATIONS

*Infant Apnea Monitors* (auth. unk.), Health Devices, Nov. 1974, pp. 3-23.
Franks, C. I. et al., "Non-Invasive Home Monitoring of Respiratory Pattern in Infants," Develop. Med. Child Neurol. 1977, 19, pp. 748-756.
Meire, H. B. et al., "Ultrasound Recording of Fetal Breathing", Brit. Jrnl. Radiology, 1975, 48, pp. 477-480.
Northrup, R. B. et al., "A No-Touch Ocular Pulse Measurement System for the Diagnosis of Carotid Occlusions", IEEE Trans. on Biomed Engr., vol. BME-24, No. 2, Mar. 1977, pp. 139-148.

*Primary Examiner*—Robert W. Michell
*Assistant Examiner*—Francis J. Jaworski

[57] ABSTRACT

Apparatus for monitoring respiratory and/or convulsive movements includes a closed loop phase lock system which measures changes in the air path length of continuous wave ultrasound transmitted to and reflected from (the chest/abdomen area of) a subject, and provides an output change signal proportional to changes in air path length caused by respiratory effort of the subject. A window/alarm circuit receives the change signal and triggers an alarm if the change signal remains below a preset lower threshold for a selected time interval, as occurs in apnea. An upper threshold may be set and an alarm triggered if the change signal exceeds the upper threshold for a selected time interval, as occurs in the case of convulsions. The apparatus includes means to provide a signal which follows movement of the subject in an unambiguous manner and which will not trigger an alarm due to extraneous (non-subject) movement. A method of monitoring movement of a subject is provided which includes transmitting continuous wave ultrasound from a source to a subject and receiving the reflected ultrasound. The method includes measuring changes in the air path length of the standing wave and providing an output signal which is proportional to the magnitude of the changes and sounding an alarm when the output signal falls outside a preselected range for a predetermined period of time.

19 Claims, 9 Drawing Figures

ULTRASONIC RESPIRATION/CONVULSION MONITORING APPARATUS AND METHOD FOR ITS USE

BACKGROUND OF THE INVENTION

The present invention concerns apparatus providing a monitoring system for monitoring respiratory and/or abnormal movements of subjects and to a method for carrying out such monitoring. More particularly, the invention pertains to a non-contact monitoring system specifically adapted to monitor respiration and/or convulsive movements of infants, although the invention is not necessarily limited thereto. A "non-contact" system means that the apparatus need not be physically connected to the person of the subject.

Generally, electronic devices for monitoring movement are known. For example, burglar alarms which employ ultrasound, i.e., ultrasonic sound waves, reflected off a moving person to trigger an alarm have been described. These devices employ the Doppler shift of the reflected ultrasound to trigger the alarm circuit. Accordingly, such devices measure movement velocity of a person or object and are incapable of reliably measuring small periodic movement such as the respiratory displacement of the chest and abdomen of a person, particularly of an infant.

Monitors specifically designed to detect infant apnea are also known. For example, see the article "Infant Apnea Monitors" in *Health Devices*, November 1974, Pages 3-23. This article deals with a number of different apnea monitors. Generally, these monitors require the infant to lie upon a special pad or mattress, to have electrodes attached to the infant's body, or to detect air flow through the mouth and/or nose of the infant by a special mask attached to the infant.

An infant apnea monitor which employed the Doppler shift of reflected microwaves was at one time on the market. However, this instrument was apparently too sensitive to nonrespiratory motions and so was deemed unreliable and subsequently discontinued from use.

U.S. Pat. No. 3,875,929 discloses the use of microwave radar to detect respiratory movement of a subject's chest and abdomen.

The use of microwave to detect infant respiration patterns is discussed in an article "Non-Invasive Home Monitoring of Respiratory Patterns in Infants" by C. I. Franks, D. M. Johnston, and B. H. Brown in *Develop. Med. Child Neurol.*, 1977, 19, pages 748-756.

The use of ultrasonic waves in diagnostic apparatus is well known in the art as is illustrated by U.S. Pat. Nos. 3,778,756; 3,830,223; 3,771,355; 3,744,479; 3,856,985; and 3,606,879. "Ultrasound Recording of Fetal Breathing" is the title of an article by H. B. Meire, P. J. Fish, and T. Wheeler in the British Journal of Radiology, 1975, 48, pages 477-480, disclosing the use of ultrasound for in utero monitoring.

U.S. Pat. No. 3,938,500 discloses the use of a piezoelectric crystal transducer positioned beneath an infant to detect any form of movement resulting from reaction to an auditory signal.

U.S. Pat. No. 3,993,995 discloses a respiration monitor based upon reflection of a sonic, optical or radio wave trained upon the subject and employing means to receive the reflected wave and to generate signals responsive to the phase difference between the reflected and transmitted waves to indicate respiration extrema.

While monitoring of respiration or other movements of a subject or patient is necessary or desirable in any number of situations, it is particularly important in connection with the care of premature and low birth-weight infants, and infants with low Apgar scores. Such infants frequently have problems with respiration, particularly in the first few days after birth. Cessation of breathing (apnea) can occur and if respiration does not resume in time, anoxia resulting in permanent damage and/or death follows. It is therefore obviously of extreme importance to reliably monitor respiration to detect apnea and sound an appropriate alarm. It is also important in many cases to detect excessive movement of a subject, such as convulsive or hyperrespiratory movement.

It is accordingly an object of the present invention to provide a novel apparatus to reliably and accurately monitor movement and lack of movement, including respiratory movement, of a subject and to sound an alarm when conditions warrant.

It is another object of the present invention to provide an apparatus for monitoring apnea in infants or other subjects, which does not require physical contact with the subject.

It is another object of the present invention to provide a novel apparatus providing a motion monitor which will respond to apnea and optionally to excessive or convulsive-type movements by sounding an appropriate alarm, and which will not sound a false-alarm caused by extraneous gross movements, such as the movement of persons attending the subject.

It is another object of the present invention to provide a novel method and apparatus for monitoring the degree of respiratory effort and, optionally, other movements of the subject by reflecting ultrasonic sound waves from the person of a subject to be monitored.

Other objects and advantages of the invention will become apparent from the following description thereof.

SUMMARY OF THE INVENTION

In accordance with the present invention, there is provided an apparatus for non-contact monitoring of movement of a subject comprising the following: an ultrasonic sound means includes generating means for generating an ultrasonic sound signal of variable frequency and transmitter means for transmitting the signal as a coherent ultrasonic sound wave to the person of a subject to be monitored, the transmitted sound wave being reflected from the subject to provide a reflected sound wave. Receiver means are positioned to receive the reflected sound wave and phase detector means are coupled to the ultrasonic sound means and to the receiver means and are adapted to compare the phase of the reflected sound wave to the phase of the transmitted sound wave, and to generate a phase difference signal therefrom. Change detection means are coupled to the phase detector means to modify the phase difference signal to generate therefrom a change signal which is proportional to changes in the length of the air path of the transmitted and reflected sound waves between the transmitter means and the receiver means. Frequency adjusting means are coupled to the generating means to adjust the frequency of the signal voltage so as to maintain substantially constant the number of wave lengths of ultrasound in the air path despite changes in the length thereof and annunciator means are coupled to the integrator circuit means to receive the change signal and thereby annunciate movement of the subject.

Certain objects of the invention are attained when the change detector means comprises an integrator circuit to integrate the phase difference signal and the frequency adjusting means is coupled between the change detector means and the generating means to define therewith and with the phase dector means a closed loop system operative to adjust the frequency of the signal voltage in response to the change signal so as to maintain substantially constant the number of wave length of ultrasonic sound in the air path despite changes in the length thereof.

In accordance with one aspect of the invention, the apparatus further includes lock-loss circuit means coupled to the integrator circuit and operative to reset the integrator circuit to cause the generating means to attain a preset center frequency when said integrator circuit approaches its saturation values. The annunciator means may include means to provide a visual display of said change signal and may further include an alarm circuit adapted to sound an alarm when the change signal does not lie within a selected range of values for a selected interval of time.

In one aspect, the invention provides apparatus for monitoring movement of a subject and comprising the following. Generating means for generating a signal voltage of ultrasonic frequency are provided, and transmitter means are coupled to the generating means to convert the signal voltage for transmission of an ultrasonic sound wave to the person of a subject to be monitored, the transmitted sound wave being reflected from the subject to provide a reflected sound wave. Receiver means to receive the reflected sound wave are included as are phase detector means coupled to the generating means and to the receiver means to receive input therefrom and to generate a difference signal indicative of the phase difference between the transmitted and reflected sound waves. Change detector means comprising an integrator circuit are coupled to the output of the phase detector means to receive the difference signal and generate a change signal indicative of transient changes in the phase difference measured by the phase detector means, the change signal being proportional to changes in the length of the air path of the transmitted and reflected sound waves between the transmitter and receiver means. Frequency adjusting means are coupled between the integrator circuit and the generating means to adjust the frequency of the signal voltage in response to the change signal so as to maintain substantially constant the number of wave lengths of ultrasound in the air path despite changes in the length thereof, whereby the change signal follows movement of the subject in an unambiguous manner. Window/alarm circuit means are coupled to the change detector means to receive the change signal, and are adapted to sound an alarm when the change signal does not lie within a selected range of values for a selected interval of time.

Certain objects of the invention are attained when the window/alarm circuit means includes threshold circuit means establishing at least one threshold voltage, and provides means for comparing the change signal to the threshold voltage to determine if the change signal lies within the selected range of values. The threshold circuit means preferably establishes both an upper threshold voltage and a lower threshold voltage and the apparatus preferably further includes a bandpass filter coupled between the integrator circuit and the window/alarm circuit to bandpass filter the change signal prior to reception thereof by the window/alarm circuit.

The present invention also provides a method for monitoring movement of a subject comprising the steps of: (a) generating a coherent ultrasonic sound wave and transmitting the sound wave to the person of a subject to be monitored for reflection therefrom to provide a reflected ultrasonic sound wave; (b) receiving the reflected sound wave to define an air path length of the transmitted and reflected ultrasonic sound wave; (c) comparing the phase of the transmitted sound wave to the phase of the received reflected sound wave and determining the difference between the respective measured phases; (d) measuring changes in the difference between the respective measured phases to provide a change signal which is proportional to changes in the air path length; (e) adjusting the frequency of the transmitted ultrasonic sound wave in response to the change signal so as to maintain substantially constant the number of wave lengths of ultrasonic sound in the air path length despite changes in the length thereof; and (f) monitoring the change signal and thereby movement of said subject. The method may further include the step of sounding an alarm when the change signal does not lie within a selected range for a selected interval of time.

DETAILED DESCRIPTION OF THE PREFERRED EMBODIMENT

Figure 1:
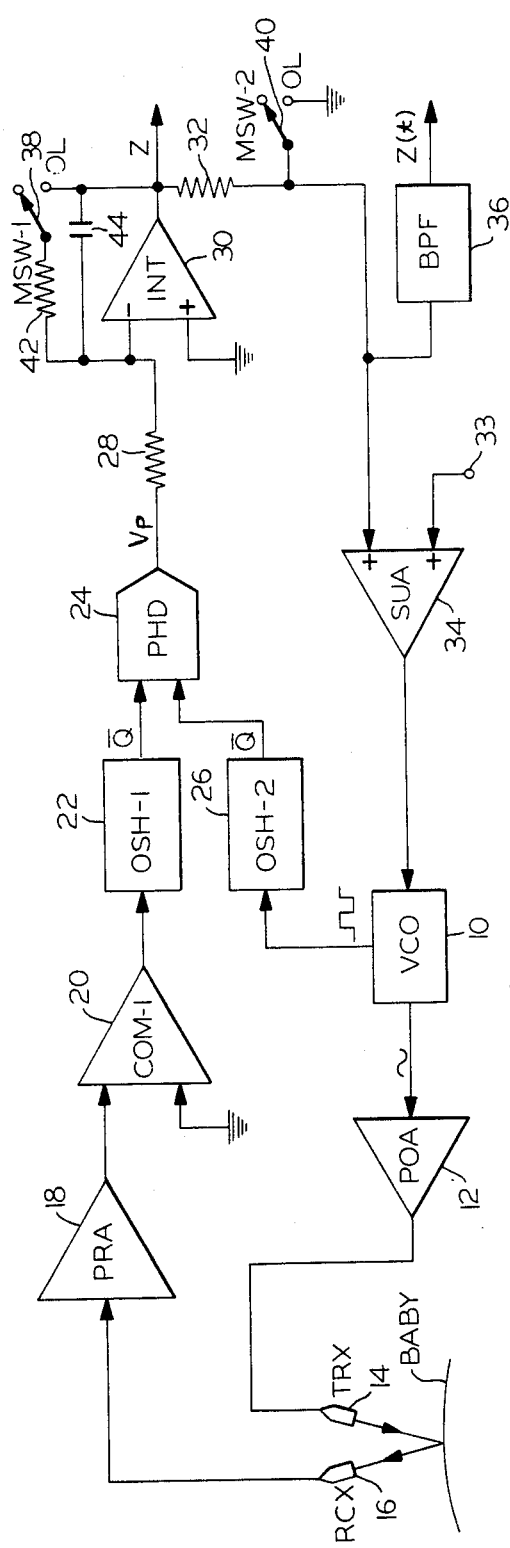
FIG. 1 is a schematic circuit diagram of an ultrasonic phase lock system of a preferred embodiment of the present invention.
Figure 8:
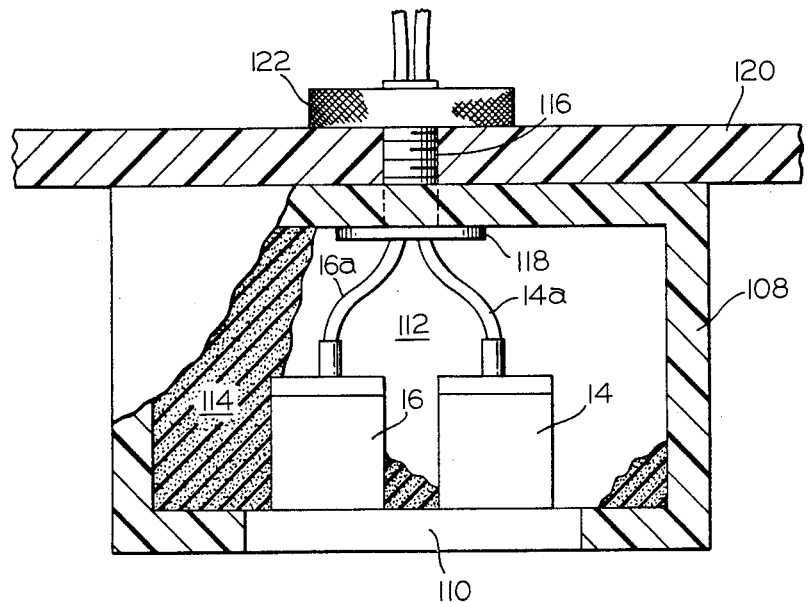
FIG. 8 is a side elevation view in section of a sensor head apparatus containing a transmitter and a receiver means and adapted for use as part of a preferred embodiment of the invention.

The phase lock system circuit of the ultrasonic phase lock apnea/convulsive movement monitor provided by the illustrated preferred embodiment is schematically illustrated in FIG. 1 and includes a voltage controlled oscillator (VCO) indicated at 10, which generates a continuous sine wave voltage of ultrasonic frequency. The continuous sine wave voltage, which may be at a frequency of 40 kHz, is coupled to a power amplifier driver 12, labeled POA in FIG. 1. Power amplifier driver 12 drives a transmitting transducer 14 (labeled TRX in the diagram) which transmits the ultrasound waves at a sound pressure level which is innocuous to the health and comfort of the subject, typically a newborn infant whose chest-abdomen area is schematically indicated by the curved line labeled "BABY", from which it is reflected to a receiving transducer 16 (labeled RCX). The path of the standing ultrasonic wave is schematically indicated by the arrows leading from TRX to BABY to RCX in the diagram. The transmitted sound pressure level of the continuous wave ultrasound is at an innocuous level, generally not more than about 73 dB (sound pressure level), reference to 0.2 nanobar, measured at 30 centimeters (or less) from transmitting transducer 14. Preferably, the transmitting and receiving transducers 14, 16 are acoustically isolated from each other in sponge rubber or other sound insulating packing and mounted close together for placement of both at a suitable distance over the chest/abdomen area of the patient, as illustrated in FIG. 8 in which there is shown one embodiment of a sensor head usable as part of the illustrated embodiment of the invention. A generally rectangular shaped receptacle 108 may be made of any suitable material such as, for example, a black plexiglas material. Transmitting transducer 14 and receiving transducer 16 are positioned side by side within receptacle 108, facing a generally rectangular opening 110 formed in one wall thereof. Transducers 14 and 16 are retained with receptacle 108, more specifically within cavity 112 thereof by any suitable sound insulating packing 114 which, for clarity of illustration, is only partially shown within cavity 112. It will be appreciated that cavity 112 is normally completely filled with packing material 114 which may be, for example, a rubberized fiber material, cotton wadding or the like. Transducers 14 and 16 may be provided by a 40 kHz ultrasonic transducer of 0.01 watts such as that produced by Calectro under its catalog number J4-815. These transducers are about 2.25 centimeters in diameter and are conveniently contained within a receptacle 108 having a depth of about 5.7 centimeters, a width of about 5.7 centimeters and a length of about 10.2 centimeters. Opening 108 is about 3.2 centimeters in width and about 6.4 centimeters in length and transducers 14, 16 are positioned about 3.8 centimeters apart (center to center) so that the sound wave transmitted from transducer 14 passes through opening 110 and the reflected sound wave received by transducer 16 similarly passes through opening 110.

Transducers 14, 16 may be mounted in place by fastener means (not shown) and/or packing 114 may serve to securely mount the transducers in place. Leads 14a and 16a connect, respectively, transmitting transducer 14 and receiving transducer 16 to power amplifier 12 and low noise pre-amplifier 18, as shown in FIG. 1. Leads 14a and 16a pass through a hollow, exteriorly threaded stem 116. Stem 116 is secured to receptacle 108 by means of a lock washer 118 or any other suitable connecting means. Receptacle 108 is mounted to a suitable support means, which in the illustrated embodiment may comprise the clear plexiglass cover 120 of an infant incubator crib, by being passed through a hole (unnumbered) formed in cover 120. A knurled lock nut 122 secures stem 116 and thereby receptacle 108 to cover 120. Opening 110 of receptacle 108 is thus supported by cover 120 and positioned thereon above the chest/abdomen area of the infant subject to be monitored. Transducers 14, 16 are preferably positioned about 30 centimeters above the infant subject's chest/abdomen area. Obviously, any suitable support means may be provided to position receptacle 108 and its transducers at a selected distance from a subject, infant or adult, to be monitored. Equally obviously, transducers 14, 16 need not be placed in relatively close proximity within a single receptacle as illustrated, but may be independently mounted in any given case as desired. For example, transducers 14, 16 may be independently mounted about 30 centimeters apart from each other to span the entire body of an infant or a larger area of the body of an adult subject. Equally obviously, different placements may be desirable for specific purposes, for example, for use with animal rather than human subjects, etc.

The transmitting and receiving transducers 14 and 16 may be relatively inexpensive crystal units such as the 40 kHz crystal units manufactured by Calectro and designated J4-815. Alternatively, Vernitron P/N 264001 air transducers resonant at 22 kHz may be employed. In a prototype unit, a tweeter loudspeaker was employed as the transmitting transducer and a high frequency condenser microphone was employed as the receiving transducer, with satisfactory results. The loudspeaker was a University Sphericon and the microphone was one manufactured by B & K, Model 4135.

The output electrical signal of receiving transducer 16 is passed to a low noise preamplifier 18 (labeled PRA). Preamplifier 18 has a gain of 15,000 and is followed by a band-pass filter (not shown) having low and high corner frequencies of 29 kHz and 43 kHz, respectively. The output signal of preamplifier 18 is passed to a Fairchild $\mu$A 760 comparator 20, labeled COM-1. The TTL output signal from comparator 20 is passed to a monostable multivibrator 22, labeled OSH-1 in the diagram. Monostable multivibrator 22 has a one microsecond dwell time and its output pulses serve as one input to a digital phase detector 24 (labeled PHD). Phase detector 24 also receives a second reference input from a monostable multivibrator 26. The input to monostable multivibrator 26 is provided by the TTL output square wave generated by voltage-controlled oscillator 10.

Phase detector 24 essentially comprises a NAND gate RS flip flop whose output states are made symmetrical about zero voltage. The output signal from digital phase detector 24 is transmitted to a resettable integrator circuit (labeled INT). The operational amplifier integrator circuit consists of the operational amplifier 30, the input resistor 28, and the feedback capacitor 44 connected between the output of operational amplifier 30 and its summing junction (inverting input). The output signal Z from the integrator circuit is passed through a line including a resistance 32 to a summing operational amplifier 34 labeled SUA in the diagram. The output signal from summing operational amplifier 34 is transmitted to voltage-controlled oscillator 10 to set its frequency as described in more detail herein below. The output signal from the integrator circuit is also passed to a band pass filter 36, labeled BPF in the diagram, to form a conditioned output signal Z(t) which is proportional to the change in the air path length from transmitting transducer 14 to BABY and back to receiving transducer 16.

A pair of MOS switches (Siliconix DG-200) 38 and 40, respectively labeled MSW-1 and MSW-2, are included in the circuit. MOS switch 38 is connected in parallel with the integrator capacitor 44 and in a line which includes a resistance 42. The capacitor 44 is connected between the output and the inverting input of the operational amplifier 30.

MOS switch 40 is connected between resistance 32 and the input to the summing operational amplifier 34 and ground. When closed, MOS switch 40 grounds the input 35 to SUA 34.

Figure 6:
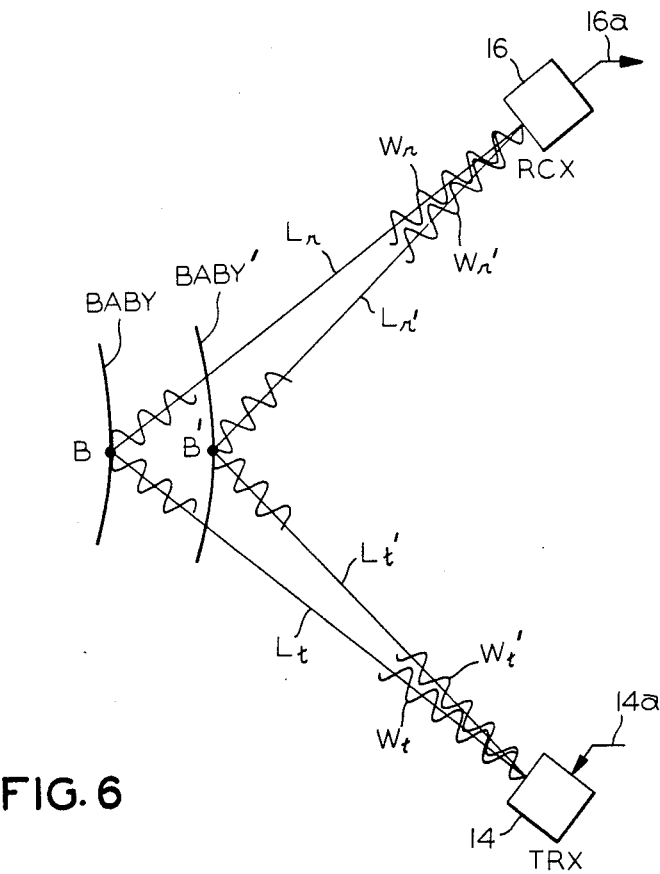
FIG. 6 is a schematic rendition on an enlarged scale of the transmitter and receiver means of the FIG. 1 embodiment, showing the subject's person in two different positions relative thereto and two resultant ultrasound air path of different length.
Figure 7:
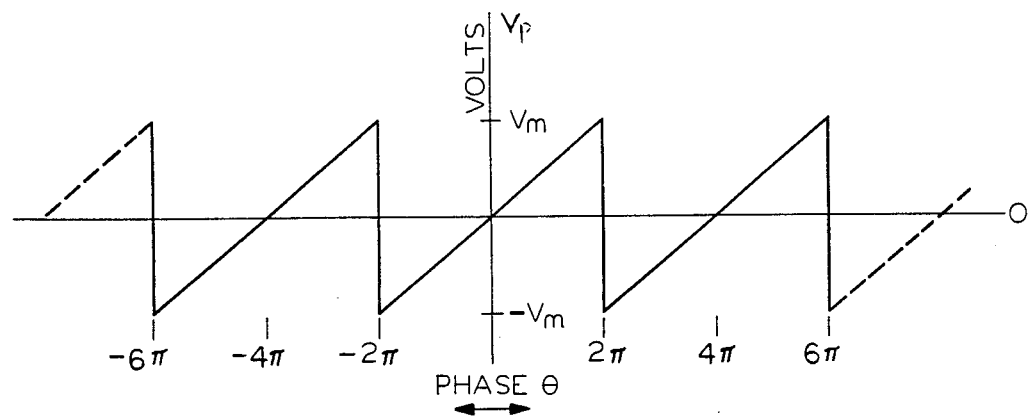
FIG. 7 is a graph plotting the input-output characteristic of a typical phase detector of the type useable in the apparatus of the present invention.

Under open-loop conditions, the output of phase detector 24 is a square wave of the frequency of the output of voltage-controlled oscillator 10 whose duty cycle, and therefore average value, depends upon the fractional wave length phase difference between the output of voltage-controlled oscillator 10 and the signal received from monostable multivibrator 22. However, phase detector 24 cannot unambiguously sense phase differences of whole wave length or greater between the reference and returned signals. In order to produce an unambiguous signal, the output of phase detector 20 is modified as described more fully hereinbelow, and a closed loop circuit is established to route signal Z to voltage controlled oscillator 10 to adjust the frequency thereof. Referring now to FIGS 6, 7, there are shown schematic diagrams which illustrate how this closed loop phase lock system of the invention provides unambiguous signaling of the subject's movement. FIG. 6 shows transmitter 14 connected by a connector 14a (to power amplifier driver 12, FIG. 1) and receiver 16 connected by a conductor 16a (to low noise preamplifier 18, FIG. 1). Transmitting transducer 14 and receiving transducer 16 are physically positioned in proximity to the subject to be monitored, say from 20 to 40 centimeters away, and preferably in a position so that the chest/abdomen area of the subject is insonified by the transmitted ultrasonic sound waves $W_t$ transmitted by transmitting transducer 14. A recommended upper limit on the sound intensity received by the subject is about 73 db above 0.2 nanobar. A portion at least of these transmitted sound waves are reflected from the person of the subject (which is illustrated by the curved line labeled BABY) as reflected ultrasonic sound waves $W_r$ to receiving transducer 16. The straight lines $L_t$ and $L_r$ show the air path length of the transmitted and reflected sound waves, B indicating the point of reflection from BABY. That is, air path length $l_o$ is equal to $L_t$ plus $L_r$. As the subject BABY breathes or otherwise moves, the point of reflection moves. A second position is indicated by B' on the curved line labeled BABY', and it is seen that the total air path length defined by the transmitted sound waves and reflected sound waves along $L_t'$ and $L_r'$ has now been shortened to $l'$. That is, $l'$, which equals $L_t'$ plus $L_r'$ is shorter than $l_o$.

Referring to FIG. 7, the input-output characteristic of a typical phase detector is illustrated. If the system illustrated in the diagram of FIG. 1 were open-loop, that is, if the output Z were not employed in conjunction with summing operational amplifier 34 and its associated DC input 33 to adjust the frequency of voltage control oscillator 10, the provided change signal Z could be ambiguous depending on the extent of movement of the subject BABY. For example, if the total phase lag due to changes in the air path length exceeds $2\pi$ radians, ambiguity exists as to the actual change of the air path length $l_o$ because of the multivalued characteristic of the phase detector. That is, the same signal would be generated by a change in air path length which corresponded to any integer multiple of $2\pi$ radians or more of lag. To illustrate: if the frequency of voltage controlled oscillator 10 were not adjusted by the closed loop arrangement, its frequency would be constant, equal to $f_o$. The total phase lag $\theta_o$ due to the air path length $l_o$ (equal to $L_t$ plus $L_r$) would be $$\theta_o = (2\pi l_o f_o)/C \text{ radians} \tag{1}$$

A reduction, $\Delta l$, occurs in the air path length when BABY is in BABY' position, as follows:

$$l' = l_o - \Delta l \tag{2}$$

The phase lag now would be $$\theta' = \frac{2\pi f_o}{C} (l_o - \Delta l) \tag{3}$$

The change in phase would be $$\theta_o - \theta' = \Delta\theta \tag{4}$$

$$\Delta\theta = \frac{2\pi l_o f_o}{C} - \frac{2\pi l_o f_o}{C} + \frac{2\pi f_o \Delta l}{C} \tag{4-1}$$

$$\theta = \frac{2\pi f_o \Delta l}{C} = \frac{2\pi f_o l_o}{C} \frac{\Delta l}{l_o} \tag{4-2}$$

$$\Delta\theta = \theta_o (\frac{\Delta l}{l_o}) \tag{4-3}$$

Therefore, if $|\Delta\theta|$ is greater than $2\pi$ radians ambiguity exists as to the actual $\Delta l$ which is implied by the value of $V_p$ in FIG. 7 due to the multivalued characteristic of the phase detector. With the arrangement of the invention, in which under closed loop conditions $\Delta\theta$ always approaches zero because of the integrator circuit in the loop, system phase error always stays close to zero. C is the speed of sound in air.

It will be appreciated that, while an integrator is preferred, theoretically at least the system would similarly work with a simple low pass filter $-K_2/(s+a)$ replacing $-K_2/s$. However, system sensitivity in the steady state, $\Delta Z/\Delta X$ will in general be different as will the dynamic performance of the system. The system likewise could function with a simple gain $-K_2$ replacing $-K_2/s$. However, closed loop stability might be a problem. The preferred form of modifying the phase difference signal is integration.

Thus, under the closed loop conditions, when the phase lock system circuit illustrated in FIG. 1 is locked, the steady-state output of phase detector 24 is a symmetrical, 50-percent duty cycle square wave with an average value of zero. During a transient change in the air path length between transducer 14 and transducer 16 caused by the breathing of BABY, there is a transient change in the duty cycle of the output of phase detector 24. Therefore, the average value of the output is momentarily non-zero. The integrator circuit integrates this average value and its output Z is used to control the output frequency of voltage-controlled oscillator 10 to keep the number of wavelengths of the ultrasound in the airpath constant in spite of the changes in airpath length due to respiratory or other movements of BABY. Under steady-state conditions, the output of the integrator circuit changes in direct proportion to small changes in the air path length between transducer 14 and 16 due to the closed loop, phase tracking behavior of the system.

The output of the integrator circuit is conditioned by band-pass filter 36 to form a conditioned output Z(t) which is also proportional to the change in the air path length. The existence of this direct proportional relationship is set forth, for example, in the article by R. B. Northrop and S. S. Nilakhe in *IEEE Transactions on Biomedical Engineering* 24: March, 1977, in an article concerning a no touch ocular-pulse measurement system for diagnosis of carotid occlusion. The disclosure of this article is incorporated by reference herein.

A DC voltage is applied to a terminal 33 of summing amplifier 34 and this voltage is added to the output of the integrator circuit. In this manner, when the loop is opened using the MOS switches 38 and 40, the voltage level provided by summing amplifier 34 sets the open-loop frequency of voltage-controlled oscillator 10.

Figure 2:
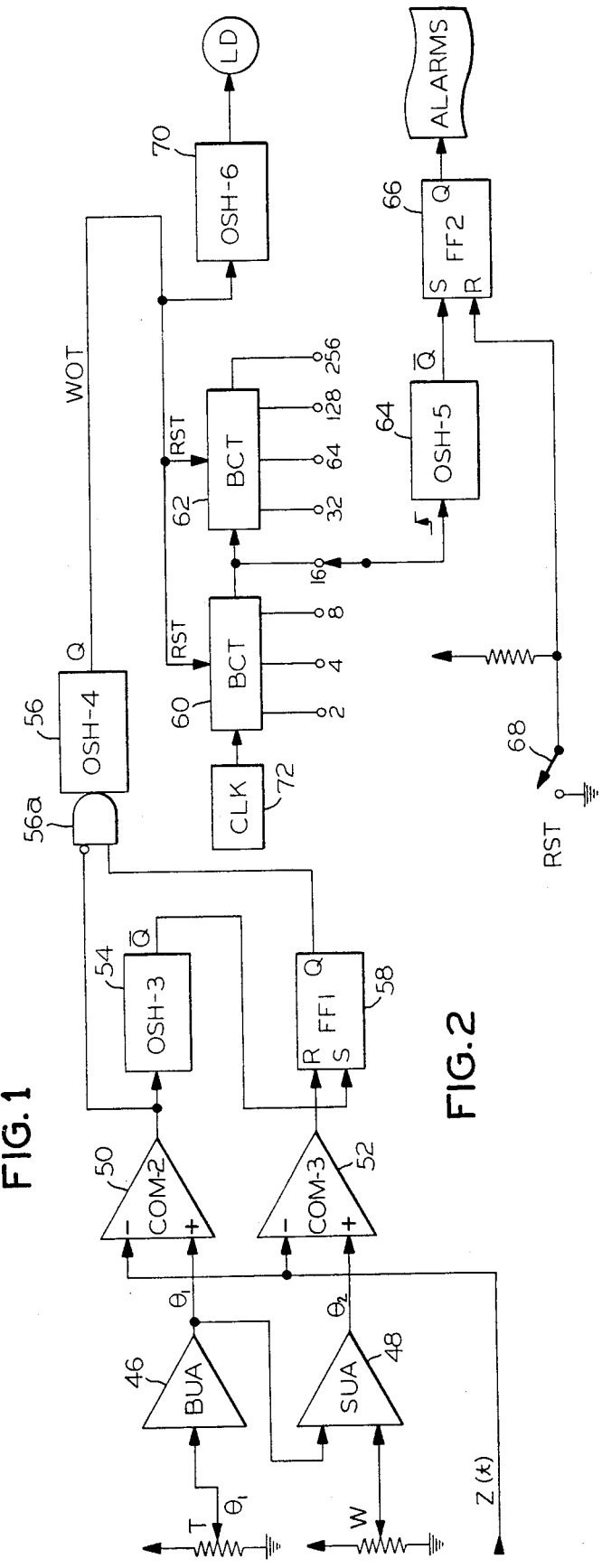
FIG. 2 is a schematic circuit diagram of the window/alarm system of the preferred embodiment.

The conditioned output Z(t) of band pass filter 36 of the phase lock system of FIG. 1 is transmitted to the window/alarm system illustrated in the diagram of FIG. 2. As indicated above, the amplitude of this signal Z(t) is proportional to the respiratory efforts of BABY, being determined by the changes in air path length between the transducers 14, 16, and BABY's abdomen and chest.

Referring to FIG. 2, a unity gain buffer amplifier 46, labeled BUA in the diagram of FIG. 2 provides a lower threshold voltage, $\theta_1$, which serves as one of the inputs into summing operational amplifier 48; the output from buffer amplifier 46 is also provided as one of the inputs to a comparator 50 (labeled COM-2). An upper threshold voltage level $\theta_2$ is provided by the output from summing operational amplifier 48 and provides one of the inputs to a second comparator 52 labeled COM-3 in the diagram of FIG. 2. The output Z(t) from band-pass filter 36 (FIG. 1) provides second inputs t, respectively, first comparator 50 and second comparator 52.

The output of comparator 50 is provided to monostable multivibrators 54 and 56, respectively labeled OSH-3 and OSH-4 in the diagram of FIG. 2. The output from monostable multivibrator 54 is provided as one input to an RS flip-flop 58 labeled FFI in the diagram of FIG. 2, the other input to RS flip-flop 58 being provided by comparator 52. The output from flip-flop 58 is provided through a gate 56a which is an integral part of monostable multivibrator 56.

Since the amplitude of the signal Z(t) received from the phase lock system circuit is proportional to the respiratory efforts of BABY, being determined by the changes in air path length between the transducers 14, 16 and BABY'S abdomen and chest, a window output pulse, labeled WOT in the diagram of FIG. 2, occurs whenever the adjusted signal amplitude exceeds the lower threshold $\theta_1$, does not exceed the upper threshold $\theta_2$, and recrosses threshold $\theta_1$ with a negative slope. The window output pulse WOT resets first and second binary counters 60, 62, each labeled BCT in the diagram of FIG. 2. A clock 72 (astable multivibrator) is labeled CLK in the diagram and provides input pulses to counters 60, 62. The clock frequency is usually set at 1 pulse/second. The window output pulse WOT resets the alarm counters 60, 62, which are continuously counting clock pulses. A third monostable multivibrator 64 (labeled OSH-5) is triggered when counters 60, 62 count a preselected number of clock pulses. If the preselected number of clock pulses is counted, it means that the window output pulse WOT has not been received for a selected time interval. This activates alarm flip-flop 66 (labeled FF-2) to operate the auditory and/or visual alarms (ALARMS). A normally-open reset push button 68 may be pressed to stop the alarms.

As indicated schematically in the diagram of FIG. 2, the number of counted pulses required to activate the monostable multivibrator 64 and alarm flip-flop 66 may be selected by switching the input to multivibrator 64 to a selected one of the outputs of counters 60, 62. In the illustrated embodiment, eight settings are provided, the increment of pulses required doubling from one setting to another and ranging from 2 to 256. In the drawing, the input is connected to a setting such that, if sixteen pulses of pulse clock 72 are counted, the alarms will be sounded.

The window output pulse WOT is also provided to a monostable multivibrator 70 (labeled OSH-6) which operates a light emitting diode LD. Light emitting diode LD flashes every time a window output pulse WOT occurs, to provide a visual indication that the system is in operation and that respiratory effort falls in the range preset by adjusting thresholds $\theta_1$ and $\theta_2$.

If the signal Z(t) does not exceed threshold $\theta_1$ then no window output pulse WOT can occur. If Z(t) exceeds threshold $\theta_1$ and also threshold $\theta_2$ before falling, the Q output of flip-flop 58 is reset to low by the output of comparator 52 going low. This inhibits gate 56a and prevents a WOT pulse from resetting the counters 60, 62 when Z(t) falls again below threshold $\theta_1$. Thus, when the signal Z(t) is less than the lower threshold $\theta_1$ (as occurs in apnea), there are no reset pulses generated. Also, if Z(t) exceeds the upper threshold $\theta_2$ (as may occur in the case of convulsive movement), no reset pulses are produced. In the absence of reset pulses, the counters 60, 62 count toward the preset number of clock pulses which will activate the alarm. The apparatus is thus capable of detecting convulsive behavior as well as apnea. If it is desired to detect apnea alone, $\theta_2$ can be raised to a maximum level which the peak Z(t) cannot attain.

It will be apparent to those skilled in the art that other arrangements could be provided to perform the function of the specific window alarm circuit described in connection with the preferred embodiment. For example, a capacitor could be continuously charged linearly towards a threshold voltage which would trip the alarm. Successive detected respirations of the subject would cause the phase lock system to produce window output pulses which are utilized to reset the capacitor voltage to zero. If respiration ceases, the production of the window output pulses ceases and the capacitor voltage rises to the alarm level. This or any other approach to provide a window alarm system triggered by cessation of window output pulses is satisfactory. The digital counter system illustrated by FIG. 2 is a preferred embodiment since it provides a relatively simple and inexpensive configuration.

As indicated above, the system of the present invention enables the detection of cessation of respiration and, optionally, the detection of convulsive movements in a system which does not require physical contact with the subject.

It is desirable that gross movement detected by transducers 14, 16, such as may occur when an attendant ministers to the subject, for example, when the diapers or other clothing of BABY are changed, not serve to trigger the alarm. This feature may be attained by the provision of an automatic lock-loss circuit as illustrated in the diagram of FIG. 3.

Generally, the lock-loss control circuit is triggered whenever the integrator output Z exceeds preselected bounds. Such excess integrator output will result from a major perturbation of the ultrasound air-path length, as when an attendant ministers to BABY. The lock-loss control opens the phase lock system loop of FIG. 1 for a selected period, such as 100 ms., during which time voltage controlled oscillator 10 is caused to oscillate at its selected "open-loop frequency" of 39 kHz set by the dc voltage at input 33 to summing amplifier 34. After the 100 ms. pause, the phase lock loop is closed; after a brief transient, the output Z of the integrator circuit will normally fall within its linear bounds and normal operation of the monitoring system will follow.

Figure 3:
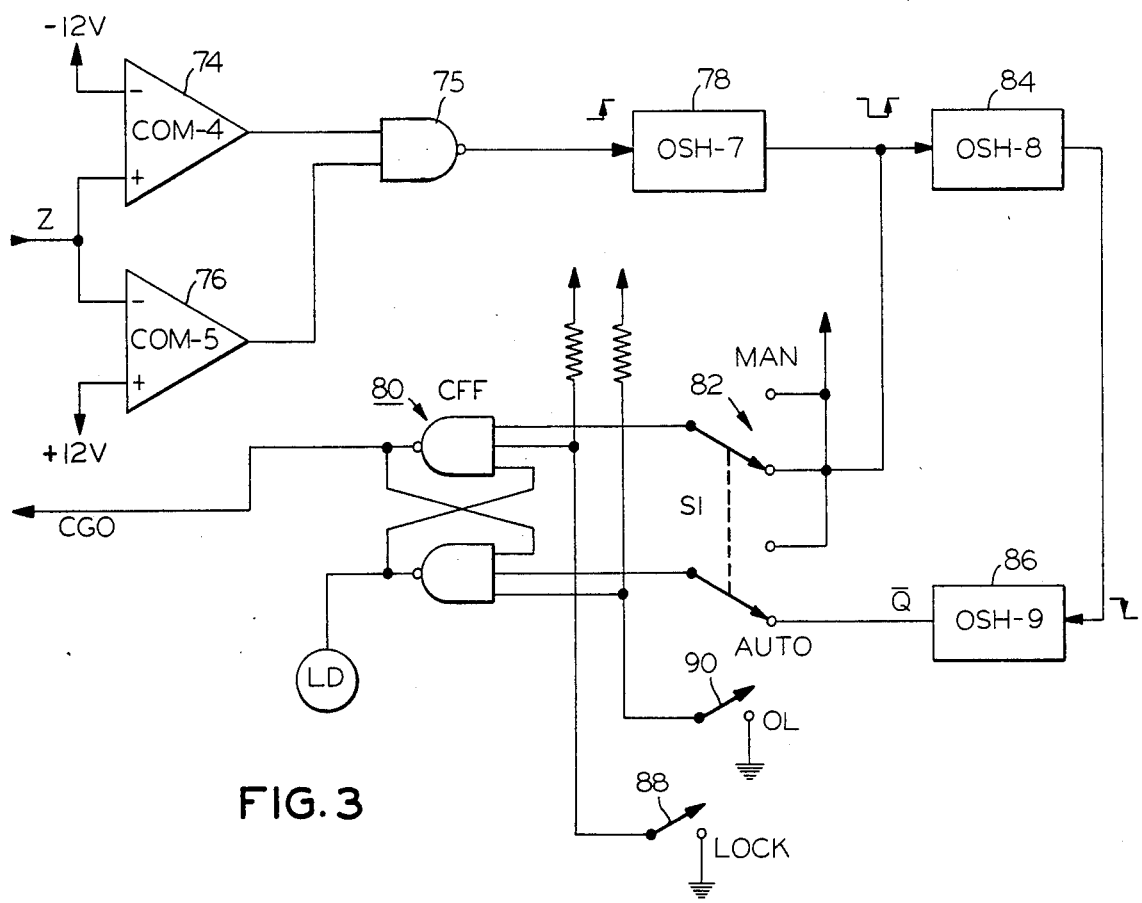
FIG. 3 is a schematic circuit diagram of the automatic lock loss control system of the preferred embodiment.

Referring now to FIG. 3, the output Z of the integrator circuit (FIG. 1) is provided to a pair of comparators 74 and 76 labeled, respectively, COM-4 and COM-5 in the diagram of FIG. 3. The outputs of comparators 74 and 76 are supplied through a NAND gate 75 to a monostable multivibrator 78, labeled OSH-7. A control flip-flop generally indicated at 80 (labeled CFF) is connected via a selector switch indicated at 82 (labeled SI) to the output of monostable multivibrator 78. If the output Z of the integrator circuit exceeds a preselected voltage, plus or minus 12 volts in the illustrated embodiment, multivibrator 78 emits a 1 microsecond complementary pulse signal to change the state of the control flip-flop 80 to high. This causes the MOS switches 38, 40 (FIG. 1) to close to the open loop position, thereby opening the phase lock system loop. The open-loop state lasts for the dwell time of monostable multivibrator 84, labeled OSH-8 in the diagram of FIG. 3, whose input is provided by the rising edge of the complementary output of multivibrator 78. The output from monostable multivibrator 86 (labeled OSH-9) resets control flip-flop 80 to low thereby opening MOS switches 38, 40 (FIG. 1) and allowing the phase-lock system loop to close. Selector switch 82 may be set to the manual position (indicated by the legend MAN in the diagram of FIG. 3) in which case control flip-flop 80 is controlled by the lock pushbutton switch 88 and open pushbutton switches 90. LD in FIG. 3 indicates a light emitting diode indicator which lights for open-loop conditions.

It will be apparent to those skilled in the art that numerous changes in components and specific layout of the illustrated preferred embodiment may be made which are nonetheless within the spirit and scope of the present invention. For example, with reference to FIG. 1, comparator 20 and monostable multivibrators 22 and 26 may be eliminated if voltage controlled oscillator 10 is of the type which has a simultaneous TTL square wave and a sinewave output, such as an Intersil 8038, or Exar XR-2206 oscillator, and phase detector 24 is a Motorola MC 4044 phase-frequency detector.

The Motorola MC 4044 phase-frequency detector accepts two periodic TTL inputs. It is designed to be actuated by the falling edges of the two inputs. The output of the MC 4044 is linear over a phase difference between the two input signals of $\pm 2\pi$ radians; it varies linearly from 0.75 V to 2.25 V. The inputs need only to be periodic TTL waveforms, hence monostable multivibrators are not required to condition the input pulses to the PHD if the MC 4044 is used.

Power amplifier 12 can be an inexpensive operational amplifier such as a Fairchild $\mu A$ 741. The preamplifier 18 should be a low noise, high gain instrumentation amplifier, for example, an Analog Devices 521 or 522. Preamplifier 18 is followed by a broad band pass filter, not shown in FIG. 1, to limit the noise in the system.

With respect to the lock loss control unit exemplified in the circuit diagram of FIG. 3, comparators 74, 76 and the NOR gate 75 could be replaced by two National LM 311 comparators with wired NOR outputs, i.e., two outputs tied together to a 4.7 K resistor to plus 5 volts. The outputs would then necessarily have to trigger the multivibrator 78 on a falling edge.

Generally, the monostable multivibrators employed throughout the system can be standard Fairchild 9602 or 74123 dual units, or 74121 single units.

Means to annunciate the change signal Z(t) are advantageously provided. The annunicator means may provide a visual readout of the signal and/or provide an audible and/or visual alarm system when movement of the subject either becomes excessive or insufficient.

Figure 5:
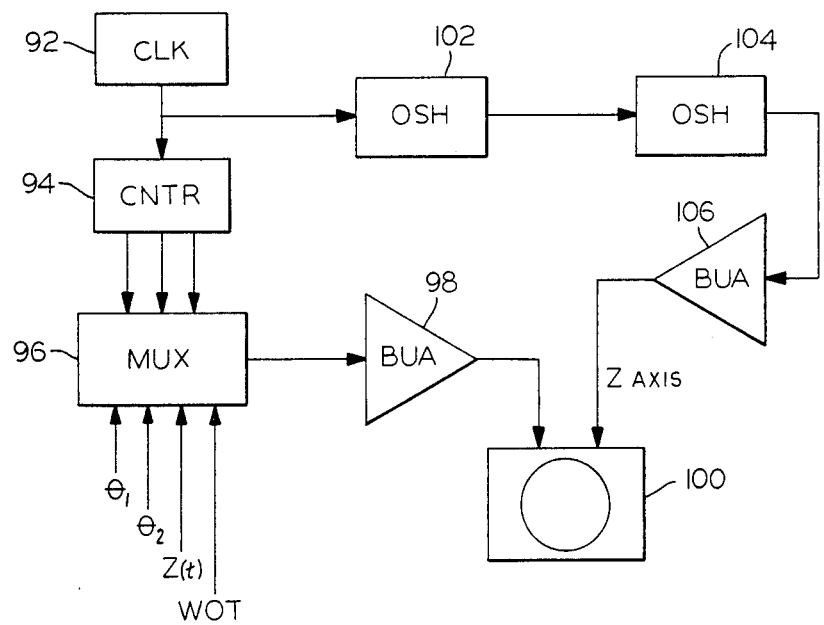
FIG. 5 is a schematic circuit diagram of a display circuit forming part of a preferred embodiment of the present invention.

Referring now to FIG. 5, a 20 KHz clock 92 (labeled CLK in the diagram of FIG. 5) imparts pulses to a modulo-8 counter 94 (labeled CNTR) which in turn provides inputs to a multiplex switch 96 (labeled MUX) which may be, for example, a Fairchild 3705 multiplex switch providing eight channels, plus or minus five volts input. Output Z(t) from band pass filter 36 of the phase lock system circuit of FIG. 1, threshold voltages $\theta_1$ and $\theta_2$, and window output pulses WOT from the window/alarm circuit of FIG. 2 are also provided as inputs to a multiplex switch 96. The output of multiplex switch 96 is provided to a buffer operational amplifier 98 (labeled BUA) and the output of amplifier 98 is provided as input to a cathode ray oscilloscope 100.

The output from clock 92 is also provided in sequence to a pair of monostable multivibrators 102, 104, each labeled OSH in the diagram of FIG. 5. The output from monostable multivibrator 104 is fed into a buffer amplifier 106 (labeled BUA) and the output from amplifier 106 provides a Z axis blanking output to oscilloscope 100. In this manner, the multiplexed analog output provided by multiplexer 96 enables the display on cathode ray oscilloscope 100 of a simultaneous record of lower threshold voltage $\theta_1$, upper threshold voltage $\theta_2$, window output pulses WOT, and change signal Z(t). The display obtained is of the type illustrated in FIGS. 4A and 4B in connection with a test of the equipment on an anesthesized rabbit.

Figure 4A:
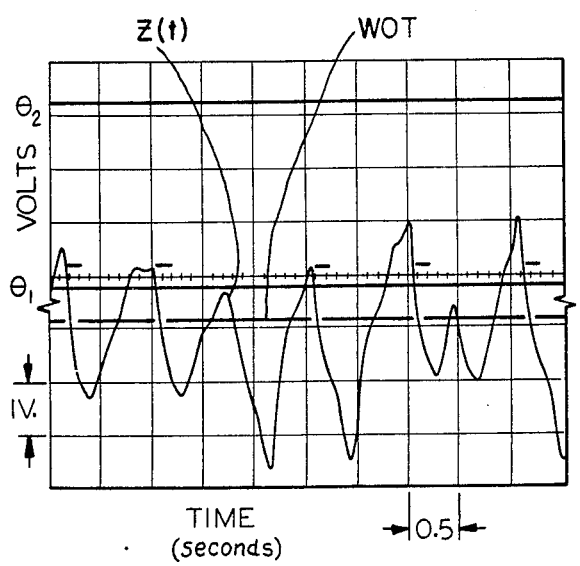
FIG. 4A is an oscilloscope display of the bandpass filtered signal of the ultrasonic phase lock system of the preferred embodiment, generated by the respiration of an anesthesized rabbit.

Referring now to FIG. 4A, there is illustrated the oscilloscope display of the window output pulses generated by the apparatus of the preferred embodiment illustrated by a rabbit anesthesized with ketamine HC1. The rabbit was a New Zealand rabbit weighing 4.5 kilograms which had been dosed with ketamine HC1 at a rate of 45 milligrams per kilogram of weight. It was necessary to cover the rabbit's abdomen with a sheet of polyethylene to reflect the ultrasound from transducer 14 to receiving transducer 16, inasmuch as it was found that the thick rabbit fur was an almost perfect ultrasound absorber at the frequencies employed.

Figure 4B:
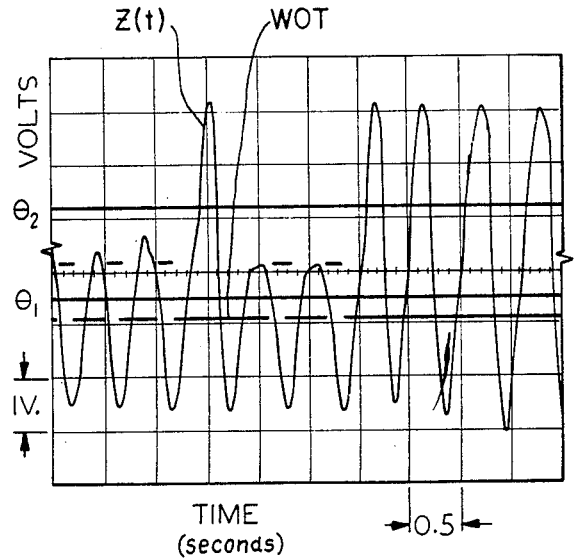
FIG. 4B is a display corresponding to that of FIG. 4A but showing the respiration of the same rabbit as the effect of the anesthesia wears off.

In both FIGS. 4A and 4B, the time base is 0.5 seconds/per unit division on the graph. In FIG. 4A, the vertical scale is 1.0 volts/per unit division and in FIG. 4B, the vertical scale is 2.0 volts/per unit division. One volt is equivalent to an air path length change of 1 millimeter.

FIG. 4B illustrates respiration of the same rabbit as the effect of the anesthesia wore off. As indicated by the trace of the window output pulses, respiration of the rabbit is more pronounced than in the readout illustrated in FIG. 4A. The breathing effort is more pronounced and certain of the peaks exceed the upper threshold. These cycles do not reset the alarm counters, and if they persist for a preselected number of clock pulses, the alarm will be triggered to indicate convulsive type activity.

The apparatus of the invention is placed in use by positioning transmitting transducer 14 and receiving transducer 16 appropriately relative to the person of the subject to be monitored. As indicated above, this is readily accomplished by positioning the transducers above the chest/abdomen area of the subject. The coherent ultrasonic sound wave is generated and transmitted to the subject to insonify the person of the subject. A portion at least of the sound waves are reflected from the subject and received by the receiving transducer. As the subject breathes or otherwise moves, the changes the air path length of the transmitted and reflected sound waves by his movement and the phase of the transmitted and reflected sound waves are compared to determine the difference between them. Changes in the recorded difference between the respective phases of the transmitted and reflected waves are measured to provide a change signal. The change signal is proportional to changes in the air path length and thereby provides a signal which in effect follows movement of the subject. The frequency of the transmitted ultrasonic sound is adjusted in response to the change signal so as to maintain substantially constant the number of wave lengths of ultrasonic sound in the air path length despite changes in the length of the air path. Thus, as the subject breathes or otherwise moves, the resulting change in air path length is noted but the frequency of the ultrasonic sound is changed to maintain substantially constant the total number of wavelengths in the path. The change signal is monitored to thereby monitor movement of the subject. An alarm may be sounded when the change signal does not lie within a selected range for a selected interval of time, and/or a visual or audible display of the same change signal may be provided. For example, an oscilloscope may be provided to provide a visual indication corresponding to respiratory effort and/or other movements of the subject.

While the invention has been described in detail with respect to a specific preferred embodiment thereof, it will be apparent to those skilled in the art that numerous alterations and modifications may be made to the specific preferred embodiment without departing from the spirit and scope of the invention; it is intended to include such modifications and alterations within the scope of the appended claims.

What is claimed is:

1. Apparatus for non-contact monitoring of movement of a subject comprising:
   (a) ultrasound source means for generating and transmitting to the abdominal/chest area of a person to be monitored coherent ultrasound whose frequency is controllable by application to said source of a control signal, the transmitted sound wave being reflected from said person to provide a reflected sound wave;
   (b) receiver means positioned to receive said reflected sound wave;
   (c) phase detector means coupled to said ultrasound source means and to said receiver means and adapted to compare the phase of said reflected sound wave to the phase of said transmitted sound wave and to generate a phase difference signal therefrom;
   (d) change detection means coupled to said phase detector means to modify said phase difference signal to generate therefrom a change signal which is proportional to changes in the length of the air path of said transmitted and reflected sound waves between said transmitter means and said receiver means, said change signal thereby exhibiting variations representing the amplitude of respiratory motion when said source means and said receiver means are aimed at the breathing person;
   (e) frequency adjusting means coupled to said change detection means to receive said change signal and coupled to said generating means to adjust the frequency of said signal voltage in response to said change signal so as to maintain substantially constant the number of wave lengths of ultrasound in said air path despite changes in the length thereof; and
   (f) window/alarm circuit means coupled to said change detector means to receive said change signal for determining whether said variations in said change signal lie within a selected range of values representative of proper respiration for a selected interval of time and for sounding an alarm when said change signal does not lie within said selected range for said selected interval of time.

2. The apparatus of claim 1 wherein said change detection means comprises an integrator circuit to integrate said phase difference signal.

3. The apparatus of claim 2 further including lock-loss circuit means coupled to said integrator circuit and operative to reset said integrator circuit to cause said ultrasound source means to attain a preset center frequency when said integrator circuit approaches its saturation values.

4. The apparatus of claim 1 wherein said frequency adjusting means is coupled between said change detection means and said generating means to define therewith and with said phase detector means a closed loop system operative to adjust the frequency of said signal voltage in response to said change signal so as to maintain substantially constant the number of wave lengths of ultrasonic sound in said air path despite changes in the length thereof.

5. The apparatus of claim 4 wherein said change detection means comprises an integrator circuit to integrate said phase difference sgnal.

6. The apparatus of claim 1 further including means coupled to said change detection means to receive said change signal for providing a visual display of said change signal.

7. Apparatus for monitoring movement of a subject comprising:
   (a) generating means for generating a signal voltage of ultrasonic frequency;
   (b) transmitter means coupled to said generating means to convert said signal voltage for transmission of an ultrasonic sound wave to the abdominal/chest area of a person to be monitored, the transmitted sound wave being reflected from said person to provide a reflected sound wave;
   (c) receiver means to receive the reflected sound wave;
   (d) phase detector means coupled to said generating means and to said receiver means to receive input therefrom and to generate a difference signal indicative of the phase difference between the transmitted and reflected sound waves;

(e) change detector means comprising an integrator circuit coupled to the output of said phase detector means to receive said difference signal and generate a change signal indicative of transient changes in the phase difference measured by said phase detector means, said change signal being proportional to changes in the length of the air path of said transmitted and reflected sound waves between said transmitter and receiver means, said change signal thereby exhibiting variations representing the amplitude of respiratory motion when said transmitter means and said receiver means are aimed at the breathing person;

(f) frequency adjusting means coupled between said integrator circuit and said generating means to adjust the frequency of said signal voltage in response to said change signal so as to maintain substantially constant the number of wave lengths of ultrasound in said air path despite changes in the length thereof whereby said change signal follows movement of said person in an unambiguous manner; and (g) window/alarm circuit means coupled to said change detector means to receive said change signal for determining whether said variations in said change signal lie within a selected range of values representative of proper respiration for a selected interval of time and for sounding an alarm when said change signal does not lie within said selected range for said selected interval of time.

8. The apparatus of claim 7 wherein said window/alarm circuit means includes threshold circuit means establising at least one threshold voltage, and means for comparing said change signal to said threshold voltage to determine if said change signal lies within said selected range of values.

9. The apparatus of claim 8 wherein said threshold circuit means establishes an upper threshold voltage and a lower threshold voltage.

10. The apparatus of claim 9 wherein said window/alarm circuit includes first means for generating a window output pulse at the conclusion of events comprising, said change signal crosses said lower threshold voltage with positive slope, does not cross said upper threshold voltage and subsequently recrosses said lower threshold voltage with negative slope, and second means for inhibiting generation of said window output pulse when said change signal crosses said lower threshold with positive slope and then crosses said upper threshold with positive slope, peaks and recrosses said upper threshold with negative slope, then said lower threshold with negative slope.

11. The apparatus of claim 10 further including an analog multiplexer coupled thereto to receive as analog inputs said upper and lower threshold voltages, said change signal and said window output pulses and having its output coupled to a cathode ray oscilloscope to display thereon a simultaneous trace of said analog inputs.

12. The apparatus of claim 7 wherein said transmitter means and said receiver means are supported above the chest/abdomen area of the person to be monitored.

13. The apparatus of claim 7 further including a bandpass filter coupled between said integrator circuit and said window/alarm circuit to bandpass filter said change signal prior to reception thereof by said window/alarm circuit.

14. The apparatus of claim 13 wherein said bandpass filter has a nominal bandwidth of from about 0.1 to 3.4 Hz.

15. The apparatus of claim 13 wherein said integrator circuit includes an operational amplifier having an input resistor connected in series therewith and a feedback capacitor connected in parallel with said operational amplifier between the output of said operational amplifier and the summing junction thereof.

16. The apparatus of claim 15 further including a lock loss circuit means coupled to said integrator circuit and operative to reset said operational amplifier thereof to restore zero initial conditions thereto and to cause said generating means to attain a preset center frequency when said integrator circuit approaches its saturation values.

17. The apparatus of claim 7 wherein said window/alarm circuit includes at least one binary counter adapted to trigger an alarm upon counting a preselected number of pulses, said binary counters being coupled to a monostable multivibrator which resets said binary counter in response to said change signal when said change signal lies within said selected range.

18. The apparatus of claim 7 wherein said transmitter means transmits said ultrasonic sound level at a sound pressure not greater than about 73 db Sound Pressure Level measured at 30 cm from said transmitter means referenced to 0.2 nanobar.

19. A method for monitoring movement of a person comprising:

(a) generating a coherent ultrasonic sound wave and transmitting said sound wave to the chest/abdominal area of a person to be monitored for reflection therefrom to provide a reflected ultrasonic sound wave;

(b) receiving said reflected sound wave to define an air path length of the transmitted and reflected untrasonic sound wave;

(c) comparing the phase of said transmitted sound wave to the phase of said received reflected sound wave and determining the difference between the respective measured phases;

(d) measuring changes in the difference between said respective measured phases to provide a change signal which is proportional to changes in said air path length;

(e) adjusting the frequency of the transmitted ultrasonic sound wave in response to said change signal so as to maintain substantially constant the number of wave lengths of ultrasonic sound in said air path length despite changes in the length thereof;

(f) establishing a predetermined range of values for said change signal representing normal breathing of said person;

(g) monitoring said change signal which represents variations indicative of the amplitude of respiratory movement of said person;

(h) comparing the value of the monitored change signal with said predetermined range of values: and (i) sounding an alarm when said change signal lies outside said predetermined range for a selected interval of time.

* * * * *